United States Patent [19]
Nappholz et al.

[11] Patent Number: 5,720,770
[45] Date of Patent: Feb. 24, 1998

[54] CARDIAC STIMULATION SYSTEM WITH ENHANCED COMMUNICATION AND CONTROL CAPABILITY

[75] Inventors: Tibor A. Nappholz, Englewood; Peter Crosby, Greenwood Village, both of Colo.

[73] Assignee: Pacesetter, Inc., Sylmar, Calif.

[21] Appl. No.: 540,416

[22] Filed: Oct. 6, 1995

[51] Int. Cl.$^6$ ............................................. A61N 1/08
[52] U.S. Cl. ........................ 607/30; 607/32; 607/60; 128/903
[58] Field of Search ............................ 128/904, 903; 607/30–32, 2, 60

[56] References Cited

U.S. PATENT DOCUMENTS

| | | | |
|---|---|---|---|
| 4,531,527 | 7/1985 | Reinhold, Jr. et al. | 128/696 |
| 4,890,621 | 1/1990 | Hakky | 128/635 |
| 4,901,725 | 2/1990 | Nappholz et al. | 128/419 |
| 5,113,869 | 5/1992 | Nappholz et al. | 128/696 |
| 5,314,458 | 5/1994 | Najafi et al. | 607/116 |
| 5,319,355 | 6/1994 | Russek | 340/573 |
| 5,342,408 | 8/1994 | deCoriolis et al. | 607/32 |
| 5,416,695 | 5/1995 | Stutman et al. | 364/413.02 |
| 5,433,736 | 7/1995 | Nilsson | 607/59 |
| 5,441,523 | 8/1995 | Nappholz | 607/14 |

OTHER PUBLICATIONS

A Low Power RF ID Transponder, Raymond Page—Wenzel Associates, RF Design, pp. 31–36.

*Primary Examiner*—William E. Kamm
*Assistant Examiner*—Kennedy J. Schaetzle
*Attorney, Agent, or Firm*—Gottlieb, Rackman & Reisman

[57] ABSTRACT

A cardiac stimulation system is provided which delivers long term cardiac therapy without a personal supervision by a physician. The system includes a cardiac stimulation device implanted in a patient and an external device in constant or periodic communication with the cardiac device. The external device is used to control the pacemaker operation. The external device receives updates of the condition of the patient and the operation of the cardiac device and the therapy provided by the cardiac device. This information is transmitted by the external device over a standard telephone network which may consist of hardwired network, a cellular network, or a combination thereof to a remote control device operating near the physician and/or a monitoring station used for monitoring and data logging information from a plurality of patients. The cardiac device, through the external device can also communicate directly and exchange information with the patient over an RF channel. Finally, the external device may be provided with ground position indication system for locating the patient geographically in an emergency.

38 Claims, 10 Drawing Sheets

CARDIAC STIMULATION SYSTEM WITH ENHANCED COMMUNICATION AND CONTROL CAPABILITY

RELATED APPLICATIONS

The subject matter of this application is related to application Ser. No. 322,852, filed Oct. 3, 1994 and entitled, "Telemetry System For an Implanted Device".

BACKGROUND OF THE INVENTION

1. Field of Invention

This invention pertains to a system that includes an implantable cardiac stimulation device. The device is permanently implanted in a patient for monitoring the patient's heart and, if necessary, for providing appropriate cardiac therapy by electrical stimulation, said therapy including, for example, synchronous or asynchronous pacing of atrium and/or ventricle, antiarrhythmic cardioversion, defibrillation, or a combination of these therapies. The stimulation device is coupled by a communication channel to an external monitoring and control device worn or carried by the patient. The external device can be used to monitor the device and through this device, the physiological condition of the heart and the status of the implant. If abnormal conditions are detected which may require professional intervention, the external device may request help from a health care professional, using, for example, a standard cellular telephone communication network. The same channel may be used by a responding physician to reprogram the implant device remotely.

2. Description of the Prior Art

Implantable cardiac stimulation and arrhythmia control devices are commercially available from several sources, including, for example, Telectronics Pacing Systems, of Englewood, Col. Typically, these devices consist of a hermetically sealed housing containing electronic circuitry for monitoring the heart of the patient and for applying electrical stimulation or electrical shock to the heart, when necessary; a telemetry device for exchanging information with the outside world; and one or more electrodes coupling the electronic circuitry and the heart. A power supply, such as a long-life battery, is the conventional energy source of the device.

The stimulation device and the associated electrodes are implanted in the patient and an external programmer is used to manipulate the parameters of the implanted device. The programmer uses two way telemetry for communication with the implanted device. After the communication link has been established, various programming options are displayed on the programmer for the physician to select the desired operating parameters. Once these parameters are selected, the programmer transmits them to the implanted device. After the programming of the stimulation device has been completed, the programmed parameters are also usually provided as the permanent record through an external printer, together with certain measured parameters. The patient is now ready to be discharged. The implanted device is checked at a prescribed follow-up visits.

The programmer is typically the shape and size of a portable personal computer, and is designed to be operated by a trained physician or health care provider. The programmer is used either in the hospital or in the physician's office.

All implantable devices have a static magnetic field detector (usually a reed switch). The detector may be activated using an external magnet to allow the physician to set the implant to a known state. For example, a pacemaker is normally set by the magnet to deliver pacing pulses at a preset rate for diagnostic purposes.

Thus, with the external programmer/internal stimulator device system, communication with the stimulation device is established only on rare occasions, i.e. during implantation and follow-up visits to the physician or the hospital, where a programmer is available. If a programmer is not available, communication is impossible. The patient cannot communicate with the stimulation device except in a very limited sense, by using the external magnet. Interaction via a magnet is not generally encouraged as the magnet sets the device to a fixed rate, a condition considered hazardous. Other communication means have been proposed but at this point remain experimental.

Commonly assigned U.S. Pat. No. 5,113,869 granted to T. A. Nappholz, et al, on May 19, 1992, discloses an implantable ambulatory electrocardiogram (ECG) monitor which acts as a warning device to transmit ECG or processed data to a remote location using a dedicated communication device.

However, there is no system presently available which can provide continuous, up to date, monitoring of implanted cardiac stimulation devices without creating an artificially encumbrant environment for the patient. Moreover there are no systems presently available which can provide communication with a patient or with a physician either in situ or remotely.

Moreover, the inventors are not aware of any system which allows a cardiac stimulation device to be monitored or reprogrammed remotely with no encumbrance to the patient, i.e., untethered monitoring.

OBJECTIVES AND SUMMARY OF THE INVENTION

An objective of the present invention is to provide a total cardiac therapy system having an implantable cardiac stimulation/monitoring device and an external control means providing substantially continuous untethered communication between the device and the patient.

A further objective is to provide a system wherein a physician can communicate remotely with the implanted cardiac device to determine the condition of the patient and the device and to update or modify the operational parameters of the cardiac device, when necessary.

Yet another objective is to provide a system which allows full mobility to the patient and utilizes an existing commercially available communication (i.e., telephone) network to enable the patient and/or the device to communicate at will with a physician, hospital or other health care facility, with the same system providing secondarily a means of communication by the patient with the implant itself.

Other objectives and advantages of the invention shall become apparent from the following description. Briefly, a cardiac stimulation system constructed in accordance with this invention includes a device for monitoring and/or stimulating the heart of a patient, hereinafter also referred to as N ICD, said device consisting of a hermetically sealed implantable housing. Inside the housing there are provided: a long life power supply for powering the device for an extended time, at least 5–10 years, an analog/digital interface circuit for exchanging signals between the device and the outside world, a microprocessor for controlling the device and a transceiver for receiving and transmitting RF range signals.

The system further includes an external unit, also called the Repeater, Programmer and Phone (RPP), for providing communication in any combination between the ICD, the patient, the physician or other health care providing facility and personnel. The external unit is preferably a cellular phone such as Motorola DPC 950 or equivalent modified as described below. The external unit includes essentially two sections: an application specific designed (ASD) telephone section for enabling standard cellular communication, and a local control section for exchanging signals with the IEP and controlling the routines specific to the added applications. The two sections communicate with each other as required and, in fact, they may share some components. The external section may include several options such as a geographic locating means for locating the external device, and hence the patient, geographically at any time. The geographic locating means may be, for example, a standard GPS (Global Positioning System) receiver. The external section may further include an ECG monitoring circuit to enable the collection and transmission of surface ECG data from the patient through standard ECG leads.

DETAILED DESCRIPTION OF THE PREFERRED EMBODIMENT

Figure 1:
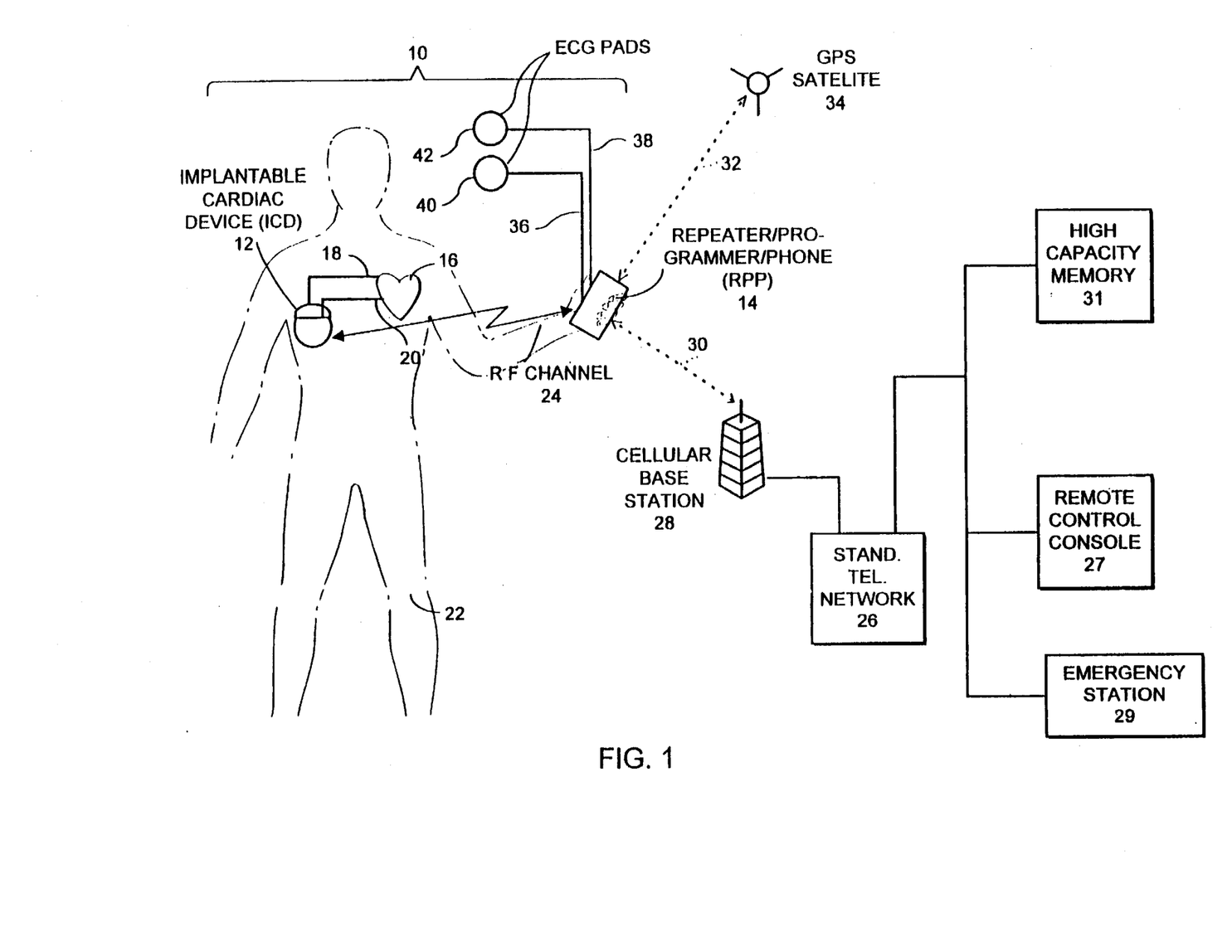
FIG. 1 shows a block diagram of a cardiac stimulation system constructed in accordance with this invention.

Referring now to FIG. 1, a system 10 constructed in accordance with this invention includes an implantable a cardiac monitoring and/or stimulation device 12 and an external device which is more specifically a repeater programmer and telephone (RPP) 14. The device 22 may be arranged and constructed to provide monitoring of the patient's heart 16, and/or to provide antiarrhythmic therapy, including antitachycardia, antibradycardia, and defibrillation. Therefore, device 12 may be referred to generically as an implantable cardiac device or ICD. The ICD 12 is implanted in a patient's body in a conventional way and is connected to the patient's heart 16.

The external unit or RPP 14 is a portable unit designed to provide comprehensive continuous or intermittent two way communication between the ICD 12 over a special RF link 24. Additionally, the unit 14 also provides communication via a standard telephone network 26 using a cellular base station 28 and the RF telephone channel 30. Through this network 26, communication may be established between the RPP 14 and a remote control console 27 and data base located at the physician's office, hospital or health care center or to an emergency station 29, such as a police or rescue squad. In addition, the RPP may be operated as a standard cellular telephone thereby providing easy access by the patient to the health care professionals and vice-versa, as well as other locations such as police, or to hold private conversations with other persons. Finally, the RPP 14 can receive continuously hiband microwave signals over a channel 32 via satellite 34 for providing global position indication, as discussed in more detail below. It should be understood that up to four such satellites may be required for complete geographic coverage.

Optionally, the unit 14 is connected via connectors and to a pair of leads terminating in ECG pads (40, 42). RPP may also communicate with a remote high capacity memory 31, as described below.

Figure 2:
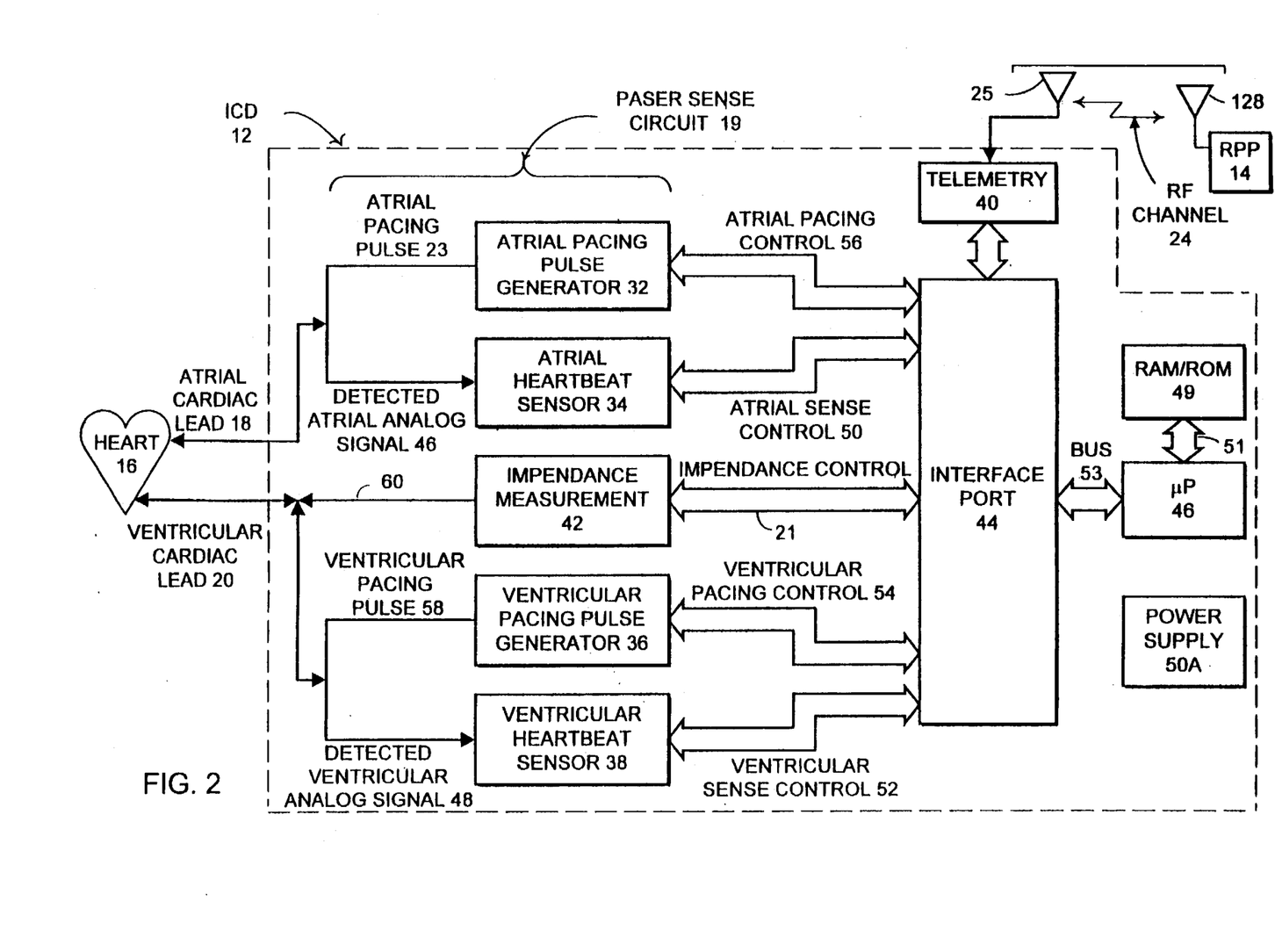
FIG. 2 shows a block diagram of the implantable cardiac device for the system of FIG. 1.

Referring now to FIG. 2, the cardiac stimulating device 12 could be for example a pacemaker, such as the pacemaker described in commonly assigned U.S. Pat. No. 5,441,523 by Tibor A. Nappholz, entitled FORCED ATRIOVENTRICULAR SYNCHRONY DUAL CHAMBER PACEMAKER, incorporated herein by reference. Device 12 may be, for example, dual chamber pacemaker provided usually with two pairs of leads 18 and 20, each being a bipolar electrode. Lead 18 extends into one of the chambers of the heart 16, for example a ventricle while lead 20 may extend into the corresponding atrium. Device 12 includes a pace and sense circuit 19 for the detection of analog signals from leads 18 and 20 and for the delivery of pacing pulses to the heart 16; a microprocessor 46 which, in response to inputs received from the pace and sense circuit 19, performs operations to generate different control and data outputs to the pace and sense circuit 19; and a power supply 50 which provides a voltage to the pace and sense circuit 19 and the microprocessor 46. The microprocessor 46 is connected to a random access memory/read only memory unit 49 by bus 51, all powered by power supply 50. The microprocessor 46 and the pace and sense circuit 19 are connected to each other by a number of data and control lines included in bus 53.

The circuit 19 includes an atrial pacing pulse generator 32, a ventricular pacing pulse generator 36, and atrial heartbeat sensor 34, a ventricular sensor 38, and a telemetry circuit 40. The preferred embodiment of the pace and sense circuit 19 also includes an impedance measurement circuit 42 for measuring a respiratory parameter indicative of the patient's metabolic demand as described in detail in U.S. Pat. No. 4,901,725 and incorporated herein by reference. The pace and sense circuit 19 further includes an interface port 44 for interfacing with the microprocessor 46 via bus 53.

In operation, the atrial and ventricular sensing circuits 34 and 38 detect respective atrial and ventricular analog signals 46 and 48 from the heart 16 and convert the detected analog signals to digital signals.

The atrial pacing pulse generator circuit 32 receives via microprocessor 46, the interface port 44, and an atrial pacing command via bus 56, an atrial pace command to generate an atrial pacing pulse 23. Similarly, the ventricular pacing pulse generator circuit 36 receives from the interface port 44, via a ventricular pacing control bus 54, a ventricular pace command to generate a ventricular pacing pulse 58.

Of course, it is contemplated that the ICD 12 may perform other functions as well. For example, the device could be an implantable cardioverter/defibrillator which senses and categorizes various atrial and/or ventricular arrhythmias, and in response, provides pacing pulses selected to correct the arrhythmia. If these pulses fail to revert the arrhythmias defibrillation therapy may be applied by the device.

The telemetry circuit 40 provides a bidirectional link between the interface port 44 of the pace and sense circuit 19 and the RPP 14 via antenna 25 on RF channel 24 as discussed below.

Figure 3:
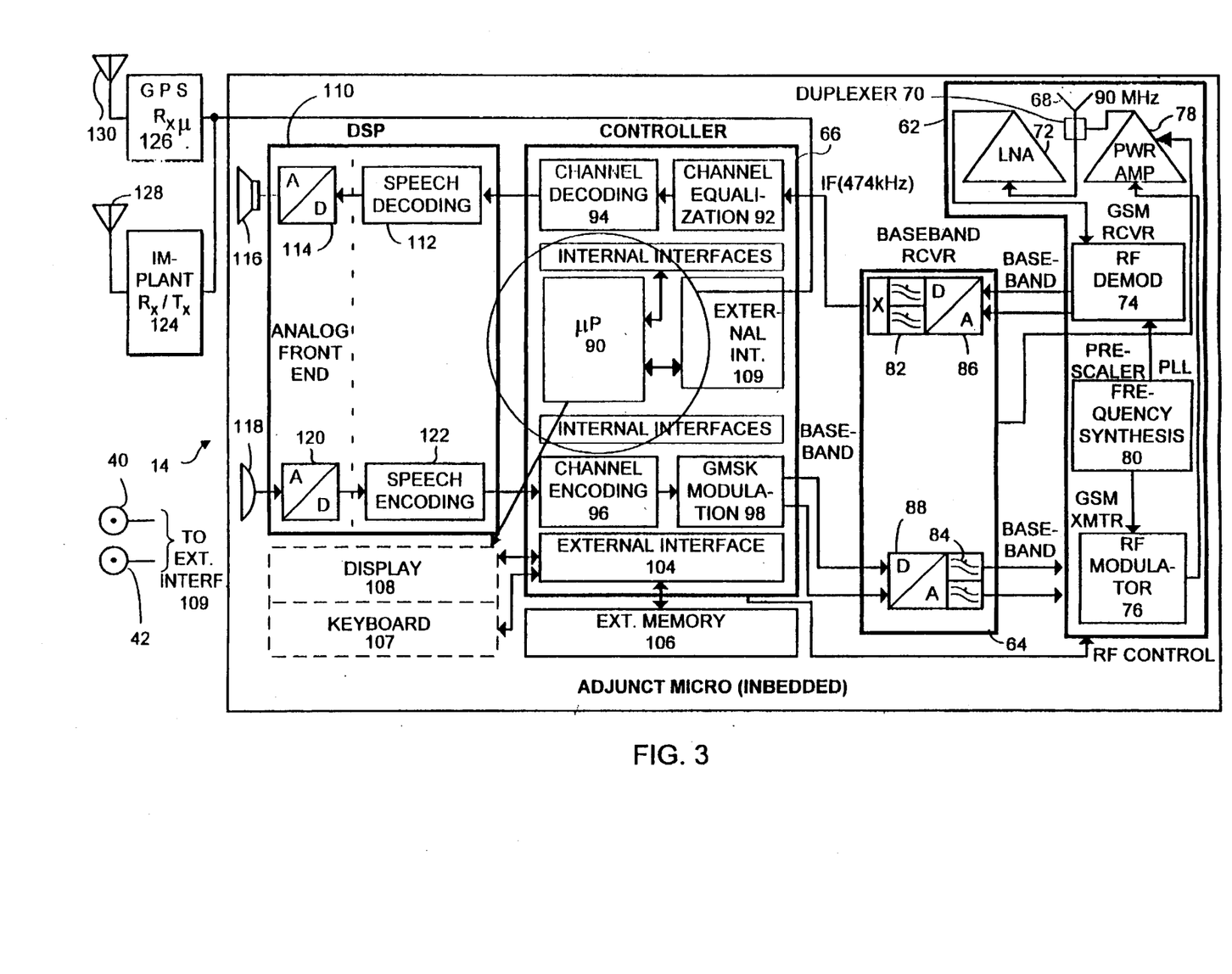
FIG. 3 shows a block diagram of the external unit of FIG. 1.
Figure 4A:
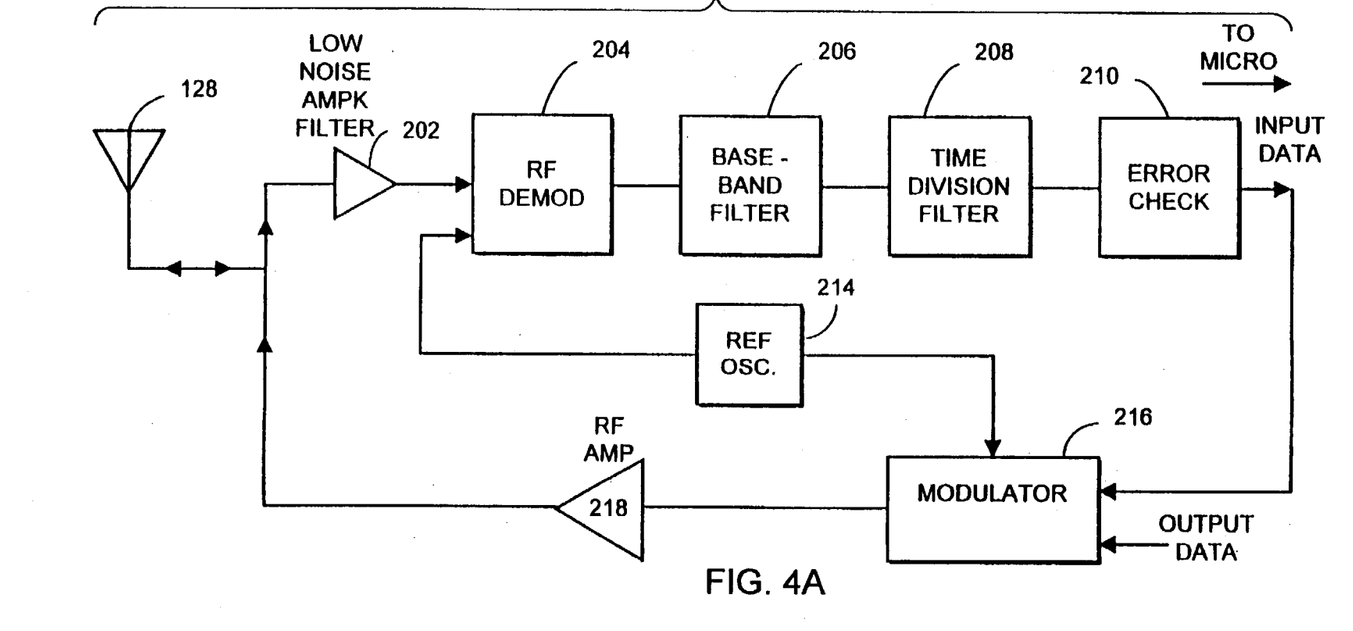
FIGS. 4A and 4B show details of some of the components of the external unit of FIG. 3.
Figure 4B:
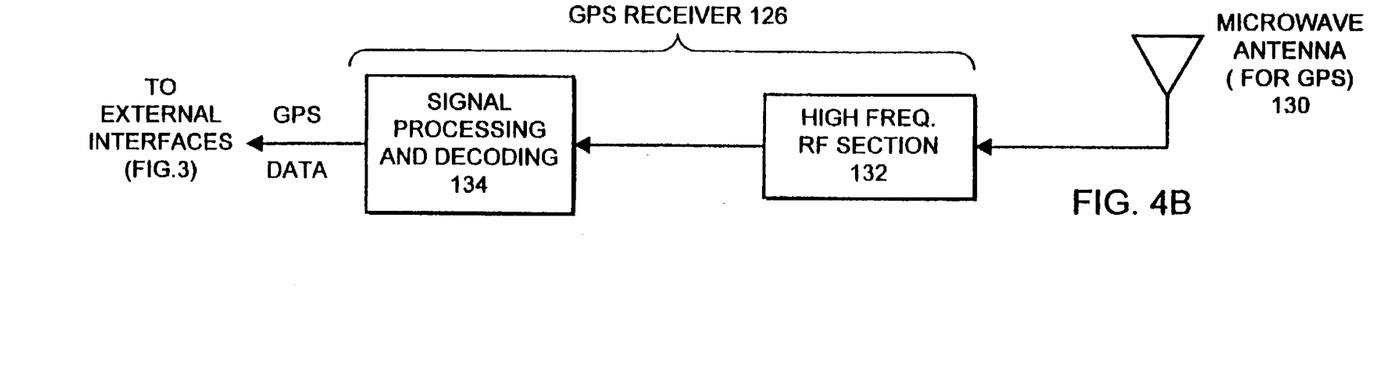

Details of the RPP 14 are shown in FIGS. 3, 4 and 4B. Preferably the RPP device 14 is a cellular telephone modified to perform some additional functions as described below. As seen in FIG. 3, external device 14 includes a radio frequency section 62, a base band section 64 and a controller 66, all being components normally associated with a cellular telephone, available for example from Motorola. Briefly, radio frequency section 62 receives and sends signals over antenna 68 compatible with the standard cellular telephone system. The antenna 68 is connected to a duplexer 70. Incoming signals from the antenna 68 are routed by duplexer to an input low noise amplifier 72. The amplified signals from amplifier 72 are fed to a demodulator 74 which in response generates incoming base band signals for base band section 64.

Similarly outgoing base band signals from base band section 64 are modulated by a modulator 76. The modulated signals, after amplification by power amplifier 78, are sent to the duplexer 70. A frequency synthesizer 80 is used to provide the mixing signals required by the modulator 76 and demodulator 74.

The base band section 64 consists of filters 82, 84, an A/D converter 86 and a D/A converter 88. The incoming base band signals are filtered and converted by converter 86 into incoming digital signals for controller 66. Outgoing digital signals from controller 66 are converted into analog signals by converter 88 and are filtered to form the outgoing base band signals.

The controller section 66 includes a microprocessor 90, a channel equalizer 92, a channel decoder 94, a channel encoder 96 and a GMSK modulator 98. The incoming digital signals are equalized by channel equalizer 92 and are decoded into received voice data by channel decoder 94. Transmitted voice data (generated as described below) is encoded by channel encoder 96 and then modulated by modulator 98 to generate outgoing digital signals. Components 92, 94, 96, 98 are controlled by microprocessor 90.

Microprocessor 90 is also connected through an external interface 104 to an external memory 106. Memory 106 is used to store programming data as well as other information required for the operation of the microprocessor 90. Microprocessor can also receive command from an operator through a keyboard 107, and display various information on a display 108. The microprocessor 90 is coupled to the keyboard 106 and display 108 through interface 104.

To complete the picture, the external device 14 further includes a digital signal processor section 110. Received digital data from the controller section 66 is fed to a speech decoder 112 and after conversion by D/A converter 114 this data is used to drive a speaker 116. Similarly, audio signals generated by a microphone 118 are converted into digital signals by an A/D converter 120 and encoded by speech encoder 122 to generate the transmitted voice data for the controller section 66.

Thus the various components described so far cooperate to perform the normal functions associated with a standard cellular telephone.

In addition, as previously described, the external device 14 also communicates with the device 12 and, optionally, with the satellite 34. For this purpose, device 14 includes an implant transceiver 124, a GPS receiver section 126 and corresponding RF antennas 128 and 130. Antenna 128 exchanges RF signals with the telemetry circuit 40 (FIG. 2) over RF channel 24. Details of the preferred embodiment for the telemetry circuit 40 are disclosed in the above-mentioned application Ser. No. 322,852, incorporated herein by reference, and are repeated below.

In a conventional approach shown in FIG. 4A, the implant transceiver 124 includes a band pass low noise amplifier filter 202 receiving signals from an antenna 128. The signals are filtered by base band filter 206. A time division filter 208 extracts the binary signals from the TDMA signals (time division multiplexed) received for the ICD 12, and after error correction by device 210.

Signals from controller 90 are used to modulate a carrier from a local reference oscillator 214 by modulator 216. The modulated signals are amplified by amplifier 218 and sent to antenna 128. Telemetry circuit 40 could be similar to circuit 128.

Details of the GPS receiver 126 for receiving microwave signals from satellite 34 are shown in FIG. 4B. Signals from antenna 130 are fed to a high frequency section 132 which translates the same into corresponding base frequency signals. These later signals are transmitted to a signal processing and decoding block 134. This block 134 in response generates GPS data indicative of the position of device 14. This GPS data is again transmitted to interface 109 for processing by microprocessor 90.

Device 14 may also include ECG pads 40, 42 which may be used to obtain a surface ECG for patient 22. These pads are coupled to microprocessor 90 through the external interface 109.

Figure 5:
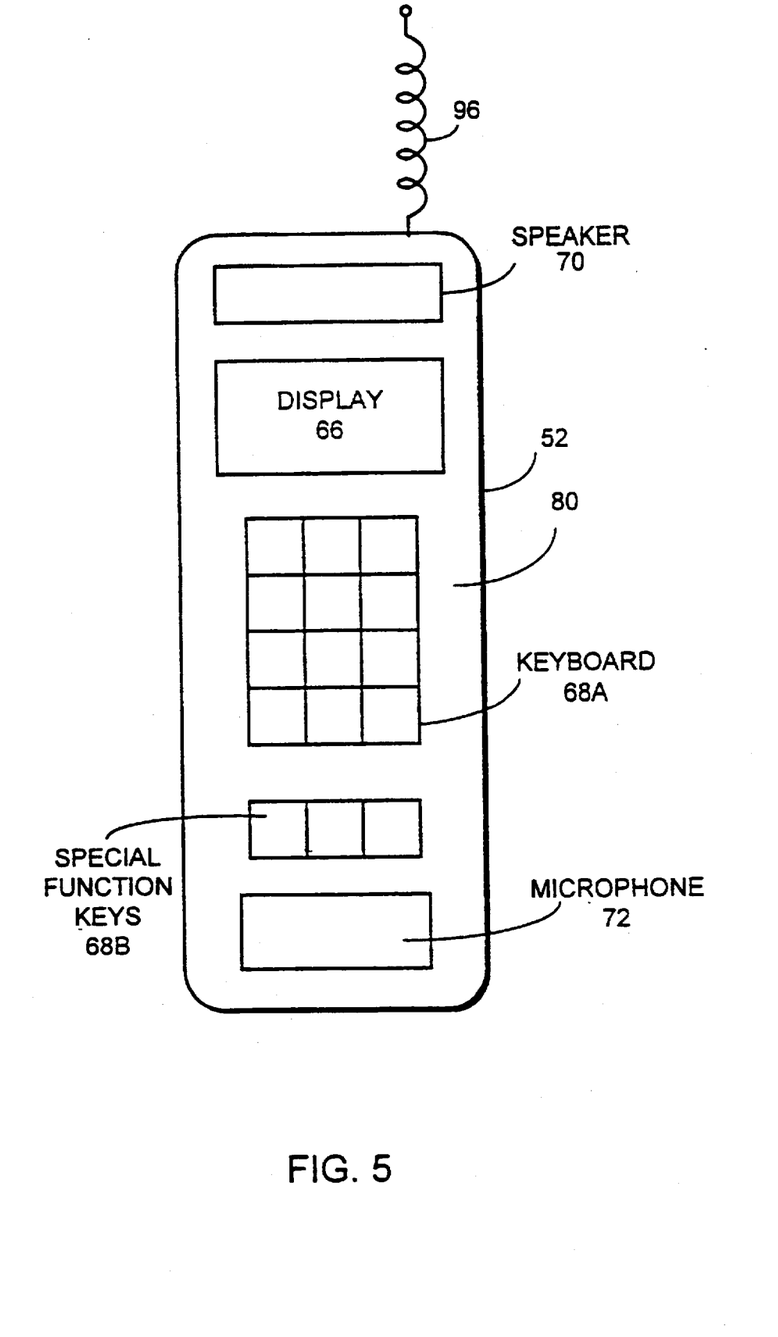
FIG. 5 shows a front view of the external device housing for communication with a standard cellular telephone network.

As shown in FIG. 5, typically, RPP 14 has a standard cellular telephone housing 52 provided with antenna 68 display 66, a speaker 70 and microphone 72. The keyboard 107 includes a standard 4×3 keypad 68A and a plurality of speed function keys 68B. Various numbers and messages are shown on display 66.

OPERATION

The system 10 can operate in several modes. These modes are discussed below.

A. Initialization and Routine Follow-up

The cardiac stimulating device 12 is provided with a variety of programmable cardiac monitoring and pacing defibrillation options suitable for a large cross-section of patients and pathologies at implant of the device 12 and the leads 18, 20 and the ICD must be customized for the patient and the disease. As mentioned above, prior to the present invention, this initialization was always performed only by a programmer.

A program required for the operation of the device 12, including a complete set of operational parameters, and allowable ranges for these parameters and other programmable options is stored in the external console 27 or RPP 14.

Programming may be done by either the console 27 or the RPP (14). At implantation it is more convenient to use the remote console 27 as it is ergonomically better designed. However there is nothing to prevent the use of the RPP 14 for the same purpose. In general in fact, what will be the case is that the RPP acts as a repeater for the remote console 27, thus emulating the wand used in conjunction with prior art programmers. At implantation, the device 12 is programmed in a conventional manner. In addition, the physician has a set of option as to what information the RPP 14 should collect from the device 12 and at what frequency, i.e., from minute to minute, day-by-day, month-by-month and so on. The RPP then proceeds to collect this information and send it to the console in the physician's office. The physician in addition has preferably an option to choose certain alert parameters and operational limits (APL). These are the parameters that will alert the physician or his staff whenever certain events occur, e.g. end of battery life EOL; electrode impedances outside limit; excessive interferences; excessive arrhythmias, etc.

If the implantation of ICD 12 occurs in the hospital or the physicians, within about 100 fee of console 27, it would be inefficient.

Instead, the remote control console 27 may be connected to a wireless 8 local access network (WLAN). Similarly, the RPP 14 may be equipped with a detachable WLAN adapter (not shown) for communication with the remote control console 27 via the WLAN.

It should be appreciated that initial programming can also be accomplished by using a conventional programmer. In either case, the device 12 is now ready to perform its function, as described below.

After device 12 has been in operation for a while, its functional parameters and programming may require changes to reflect hardware changes, such as, for example, in the impedance of the interface between the heart tissues and the leads 18, 20, or changes in the pathological conditions/characteristics of the patient.

Figure 6:
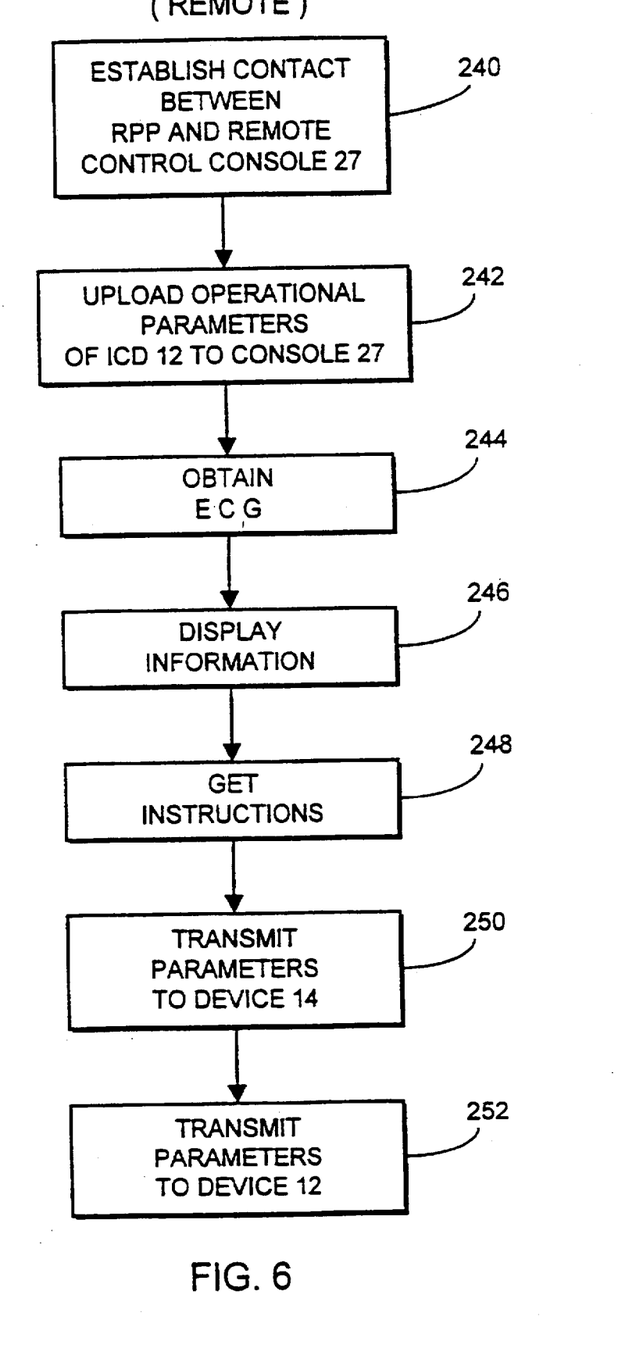
FIG. 6 shows the flow chart for changing remotely the operational parameters the implantable cardiac device of FIGS. 1 and 2.

An important feature of the present invention is that the operation of the cardiac stimulation device may be modified remotely. This mode of operation is shown in FIG. 6. First, in step 240, communication is established between the RPP 14 and the remote control console 27. In FIG. 1, the remote control device 27 is shown connected directly to the standard telephone network. However, it should be understood that device 27 could also be a cellular-type communication device, in which case the connection to the standard telephone network is accomplished indirectly through a second cellular link. The NWPM 27 is preferably a standard network programmer.

Once communication is established, in step 242, the operational parameters of the device 12 are uploaded to device 27. In step 244, an ECG is obtained, if necessary. Since this operations carried out remotely, the patient may be asked to install the contact pads 40, 42 himself. The ECG is also uploaded to the remote control console 27. Alternatively an internal cardiac ECG can be taken by device 12.

In step 246, the information obtained in steps 242 and 244 are displayed in a manner compatible with device 27.

In step 248, the physician enters instructions for the initializing or changing the functional parameters. In step 250 the functional parameters are downloaded to external RPP 14.

In step 252, the functional parameters are downloaded from RPP 14 to the cardiac stimulating device 12.

B. Normal function

After initialization or modification, the cardiac stimulation device 12 is ready for operation. While the device 12 performs its designated function, the patient is always in the vicinity of the RPP 14. For this purpose, the RPP 14 may be provided in a holster worn by the patient. During a rest period, or at night, the RPP 14 may be left on a night table or other support surface disposed adjacent to the patient. In all these arrangements, care must be taken that the distance between the device 12 and RPP 14 does not exceed the ranges of the telemetry device 40 and implant transceiver 124.

At preset intervals varying, for example, from five minutes to several months, a handshaking takes place between the RPP 14 and device 12. This hand-shaking may be very simple, consisting merely of a confirmation by the device 12 that it is operating properly. However, preferably, during this hand-shaking protocol, the device 12 also unloads to RPP 14 various information stored in the RAM 49, like its current and long term pacing parameters, as well as the other APL parameters previously discussed.

Similarly, at regular intervals, for example, every twenty-four hours, the RPP 14 performs a handshaking protocol with the remote control console 27 and/or memory 31. Memory 31 may be for example a large digital storage facility used to monitor several patients and to collect information from each patient concerning their status, current operational parameters, ECGs and so on.

In this manner, a continuous record is generated of the operation of each device 12, as well as the condition of each patient associated with the device 12. In addition, the initialization and modification of each device can be similarly recorded by the console 27, including date, time, the person performing the modifications, how the parameters were changed and so on. This record provide important archival information.

An important feature of the invention is that it provides full access by the physician to the device 12 from a remote location. The physician can review the data in the console 27 at regular intervals. Interaction with the occurs preferably only when an APL alarm is set or the patient/physician is concerned. Therefore, the patient may schedule an appointment for a check-up by telephone. At the appointed time, the patient calls up the doctor and answers typical questions about his health, level of activity and so on. This conversation may take place over the cellular telephone portion of RPP 14. The physician then accesses the device 12 through the RPP 14 and reviews its various operational parameters as well as patient characteristic information. For example, the physician may upload to his remote control console 27 a series of ECG charts taken over an extended time period, as well as other characteristics such as impedance measurements, long term minute volume variations and so on. After reviewing and analyzing this information, the physician may change the operational parameters and download them through RPP 14 to device 12 as shown in FIG. 6. This whole process takes place while the patient is in his home, office, or practically anywhere he chooses to be. Similarly, the physician may be in his office or anywhere else because the communication between them is established thorough the cellular telephone system.

C. Pathological and Physiological Dynamic Changes

The purpose of most implantable cardiac stimulation devices is to perform dynamic cardiac therapy in such a manner that the patient can live a normal life. In practical terms, this means that the cardiac stimulation device must be adaptable to various physiological or pathological conditions and to vary the therapy applied to the patient accordingly. One of the biggest obstacles facing pacemaker designers is the determination of the source of a change in physiological parameter, such as, for example, the heart rate. The heart rate of a patient may go up suddenly because he starts exercising, because he has taken some medication or consumed some specific food which has a specific effect on him, because of high altitude, or because of physiological or psychological stress. Some cardiac stimulation devices are able to track a physiological parameter such as minute volume variation, which may be indicative of the actual metabolic demand of the patient's body. Thus, if the pacing rate increases, an assumption is made in these devices that the patient is engaged in physical exercise, and the heart can be paced at a faster rate, accordingly. However, such a determination is difficult to make if the heart is arrhythmic or fibrillating because of a pathological condition due to the fact that the IDC could not communicate directly with the patient.

An advantage of the present invention is that it allows direct communication between the IDC and the patient.

In accordance with the present invention, in Step 300 (FIG. 7), when the device 12 detects a change which may require a different mode of operation, it establishes communication via a routine handshake. The device 14 then requests information from the patent about his level of activity. Various levels of activity are displayed, as shown in Step 302. This is accomplished by showing a menu of activities on display (Step 302). In Step 304, the patient selects a key on unit 14 corresponding to his level of activity, the device 12 then reconfigures or modifies its operational parameters, in Step 306.

Figure 7:
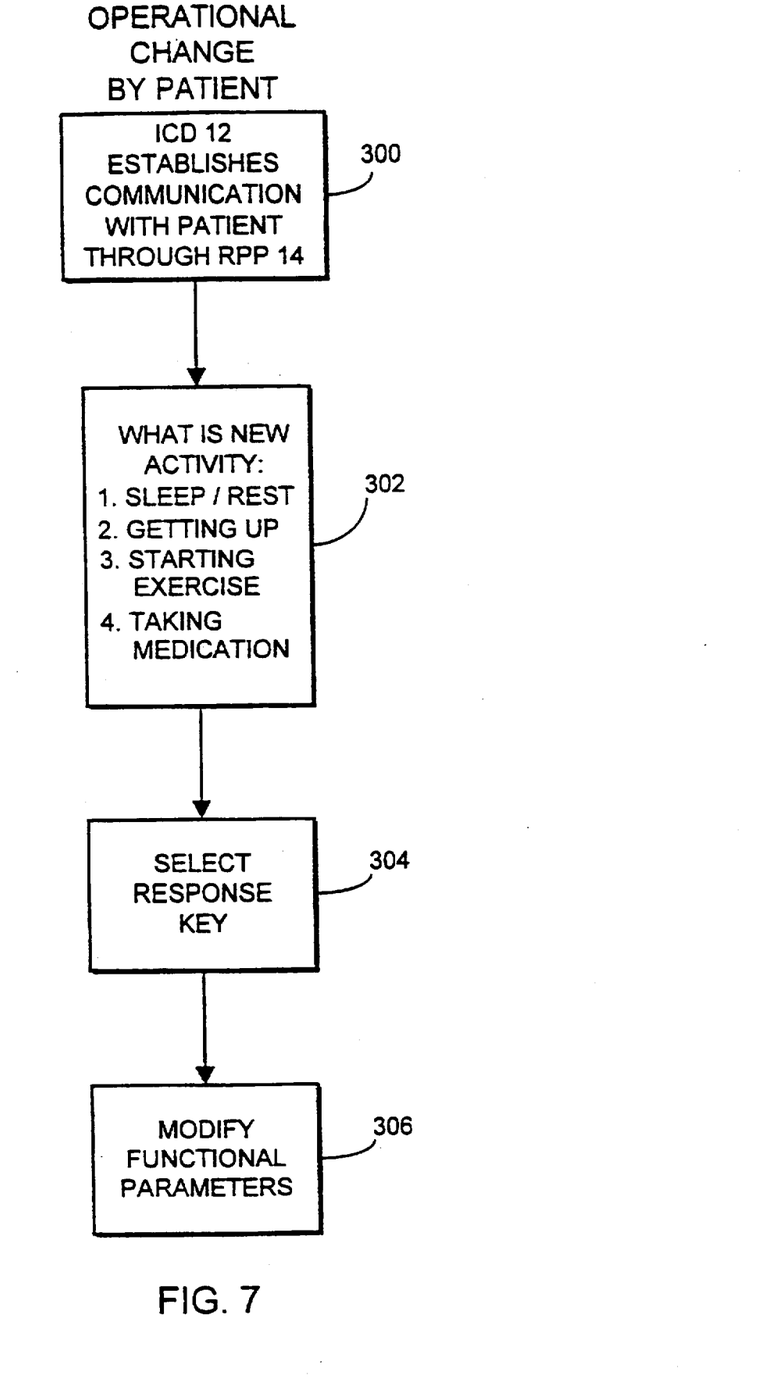
FIG. 7 shows a flow chart for changing the operation of the device by the patient.

In certain cases the implant could do a spot check, because the pacing rate has done something suspicious, e.g.; stayed high for a while, is intermittent, etc. In cases like this the implant would ask the patient what is happening or happened at a certain time. Many patients take medication that effect heart functions; rate, refractory, arrhythmias, etc. In these cases the change measured by the implant could be used to alert the patient to limit his activity to comply with the respective drug.

The device 12 may also use the channel 24 to alert the patient of a change in its mode of operation. For example, normally a dual chamber pacemaker may be operating in a synchronous mode wherein each ventricular pacing is preceded by an atrial pacing (intrinsic or forced), referred to as a DDD or DDDR mode. However, in case of atrial fibrillation, this synchrony is lost, and the device 12 may switch to a VVI or VVIR mode wherein the atrial pacing is ignored. This change in the mode is probably sensed by the patient and may be a source of concern. In this case persisting atrial fibrillation is detrimental to the patient and the physician may want this rhythm reverted. In such a case the patient would be alerted and asked to go to a medical center to have the arrhythmia reverted.

In order to accomplish this function, device 12 may establish communication with the patient as described above, through channel 24 by providing first a beep through speaker 70 and then providing an appropriate written and/or voice message to let the patient know that (a) an atrial fibrillation has been detected and (b) the device has switched to a new mode of operation. In this manner, the patient is fully informed of what is happening and comforted that appropriate therapy is being administered. Of course, a message is also sent by device 14 to the device 27 and/or 29 to announce a new mode of operation and what caused the change. When the atrial fibrillation ceases, the device 12 reverts to its former operational mode. This change is again announced to the passenger and the remote derives 27, 29.

D. Emergencies

As noted, the primary function of the cardiac stimulation device 12 is to monitor the heart of the patient and to provide appropriate therapy to insure that the heart is beating in a manner commensurate with the patient's requirements. Depending on the structure and operation of the device, the therapy may range from dual chamber synchronous pacing, to antiarrhythmic pacing, and finally, if these stimulations are unsuccessful, to defibrillating. However, even with this advanced automatic therapy options, the patient's heart may still experience a catastrophic pathological state for which the repeated fibrillation is ineffective. In this case, device 12 sends an emergency message to RPP 14 requesting help. In its turn, RPP 14 sends out an emergency message to either the remote control 27, or some the emergency station 29 via the standard cellular network. Alternatively, the RPP 14 may contact the police or the nearest hospital/emergency room. RPP 14 may also attempt to contact the patient through the speaker to determine of the patient can provide sufficient information regarding his location for the emergency service. If the patient is unable to provide this information, the RPP 14 then accesses the Global Positioning System (GPS) 76. The GPS 76 periodically receives high frequency signals from a satellite 34 via RF channel 32. These signals are used by the GPS 76 to determine geographically the position of RPP 14. This position is provided to microprocessor 90 which then transmits it to the agency providing the emergency medical service. In this manner, the patient can receive timely assistance even if he is unconscious.

Advantageously when the RPP 14 is not being used for any operations related to the device 12, the patient is free to use it as a standard cellular telephone for his personal communications.

PREFERRED EMBODIMENT OF THE CHANNEL 24 AND TELEMETRY CIRCUIT

Preferably channel 24 between implant 12 and RPP 14 is a passive channel, wherein the implant includes a passive transponder which does not by itself radiate RF signals but rather selectively reflects them from an external transmitter, i.e., an RPP. A system incorporating such a preferred passive channel is described in the above-mentioned co-pending application Ser. No. 322,852 entitled TELEMETRY SYSTEM FOR AN IMPLANT DEVICE. This passive channel shall now be described in more detail for the sake of completeness, it being understood that it does not form a part of the present invention.

Figure 8:
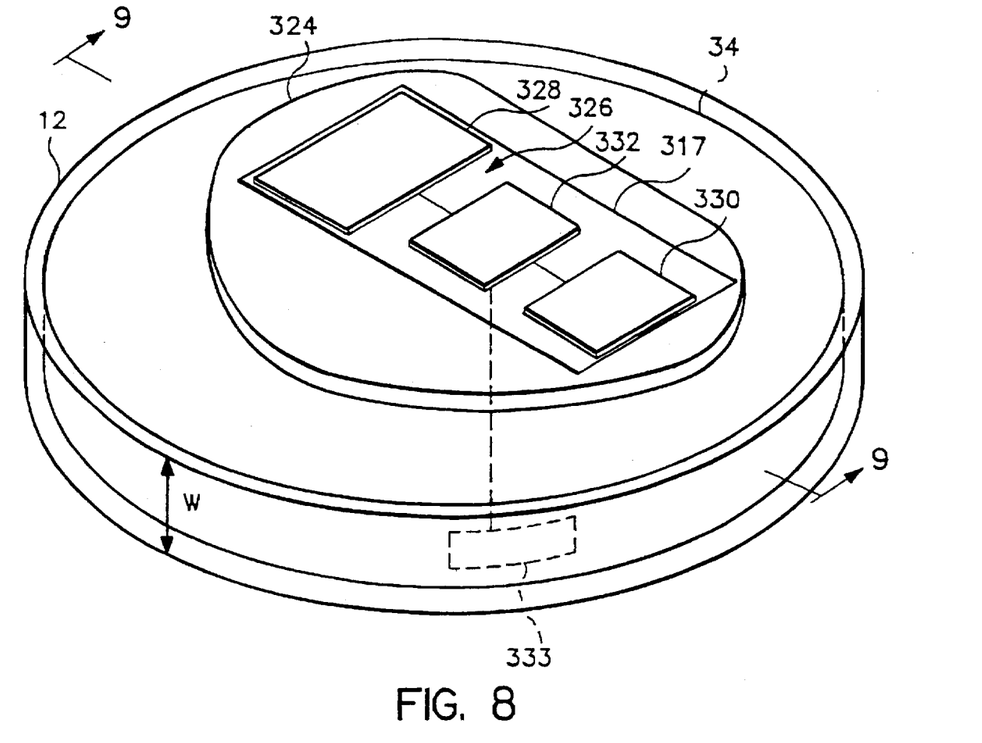
FIG. 8 is a perspective view of the implanted device showing the placement of a passive transponder thereon.

FIG. 8 shows a perspective view of the implanted device 12. The transponder 317 is disposed on a high dielectric substrate 324 attached to one or more outer surfaces of the implanted device 12. The transponder 317 includes transponder circuitry 326 having to a signal receiving antenna 328 for receiving signals transmitted from the RPP 14, a signal transmitting antenna 330 for transmitting information signals back to the RPP 14 and circuitry 332 disposed therebetween. FIG. 8 also shows that the transponder circuitry 326 receives signals from the pacemaker circuitry 333 disposed inside of the implanted device 12 as shown in more detail in FIG. 2.

FIG. 8 depicts one embodiment of the invention wherein the implanted device 12 is a disk-shaped pacemaker. This pacemaker has a thickness w of about 7 mm.

An important feature of the invention is the arrangement of the antennas 328 and 330 with respect to the implanted device 12 and with respect to each other. Another important feature of the invention is the type of antenna employed. In the preferred embodiment, the antennas 328 and 330 are microstrip antennas. This type of antenna conforms easily to the outer surface of the implanted device 12, thereby minimizing the amount of thickness added to implanted device 12. Also, this type of antenna can be attached to a very thin substrate on the device 12 and readily accepts an optional bio-benign protective coating.

As described more fully below, the microstrip antennas 328 and 330 may operate at different frequencies. Thus, interference and clutter are potential problems. To improve interference suppression and clutter discrimination, the antennas 328 and 330 are oriented so that their respective polarizations are orthogonal or perpendicular to each other.

Figure 9:
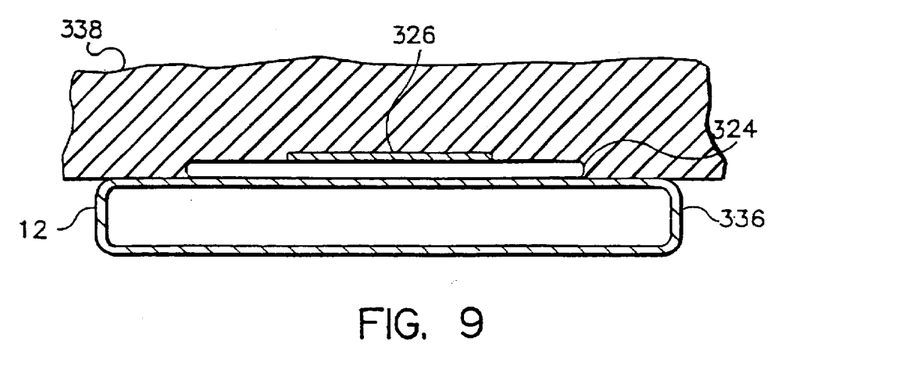
FIG. 9 is a secitional view of FIG. 8, taken along lined 9—9 in FIG. 8.

FIG. 9 is a sectional view of the implanted device 12 shown in FIG. 8, as the device 12 appears when unplanted inside the patient. This view shows the device's metal case 336, dielectric substrate 327, transponder circuitry 326 disposed on the substrate 324, and the patient's biotissue 383.

The transponder circuitry 326 may have an optional biobenign coating thereon (not shown). The relative width of the substrate 24 with respect to the overall width of the case 336 is substantially exaggerated for illustration purposes.

Figures 10A, 10B:
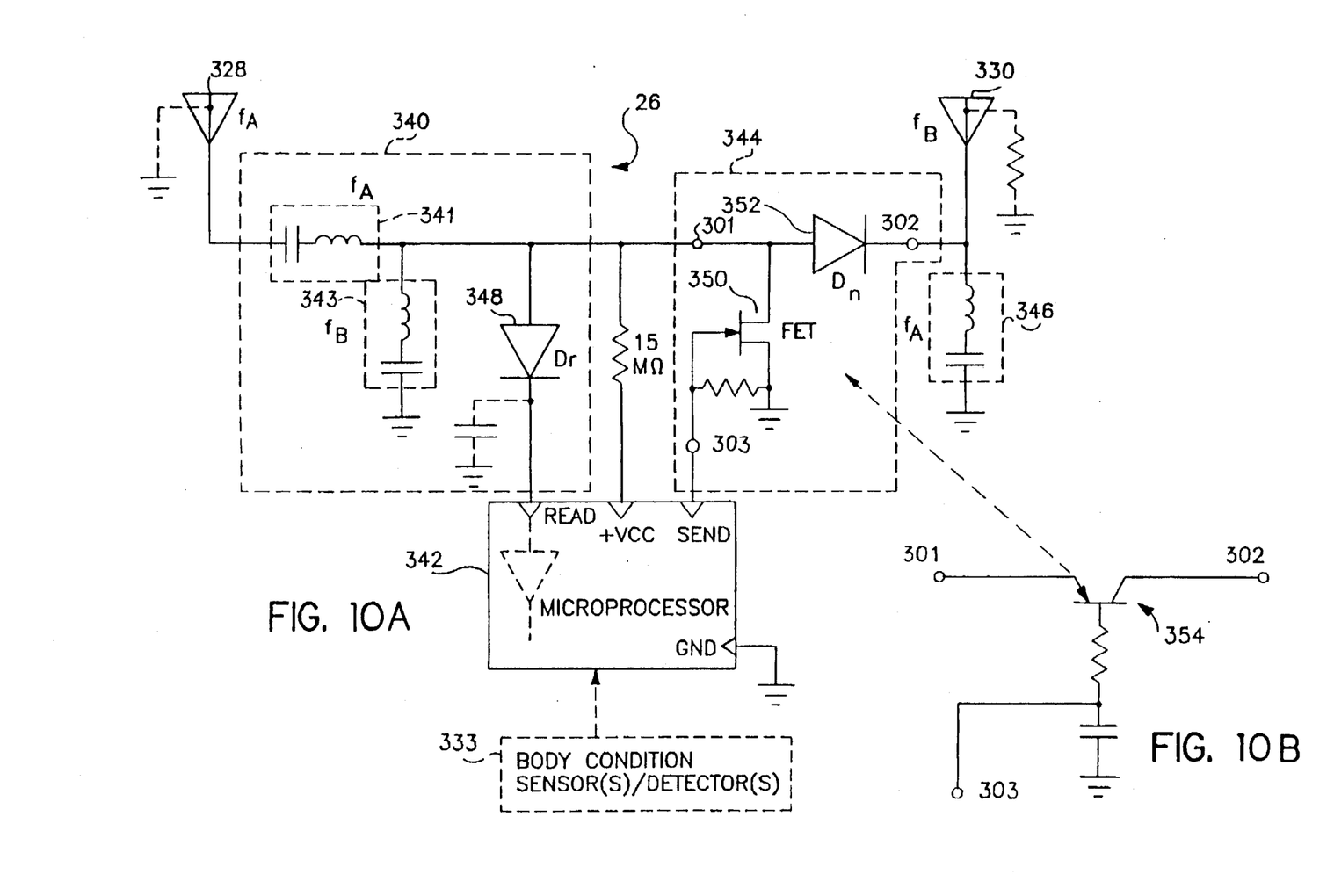
FIG. 10A is a schematic diagram of a transponder circuit associated with the implanted device according to a preferred embodiment of the present invention.
FIG. 10B is a schematic diagram of a portion of the transponder circuit for replacing a portion of the circuit shown in FIG. 10A, according to an alternative embodiment of the present invention.

FIG. 10A shows a schematic diagram of the transponder circuitry 326 of the implanted device 12. To operate as described below, the transponder circuitry 326 preferably includes at least the following six main sections:

1. signal receiving antenna 328;
2. filtering and rectifying section 340;
3. microprocessor 342;
4. a harmonic generating and modulating section 344;
5. signal transmitting filtering section 346; and
6. signal transmitting antenna 330.

The microprocessor 342 could be a separate microprocessor or could be identical to microprocessor 46. It is not necessarily a physical part of the transponder circuitry 326, although it is part of the implanted device 12. For cost-effective implementation, it will be more desirable for the transponder circuitry 326 to time-share with the microprocessor associated with the prior art heart rhythm detection and processing circuitry (which is already disposed in the device's case 336). Such a microprocessor 342 typically includes an interrogation mode which "wakes it up". That is, when an appropriate identification signal is received by the microprocessor 342, it becomes fully functional and sends out information signals related to monitored body conditions (e.g., heart rhythm data, if the implanted device 12 is a pacemaker).

In this embodiment, signal lines connect the microprocessor 342 disposed in the device's case 336 to the remaining parts of the transponder circuitry 326 attached to an external surface of the case 336.

Alternatively, the microprocessor 342 is a dedicated device which is physically part of the transponder circuitry 326. In this embodiment, the microprocessor 342 is disposed on the substrate 324 with signal lines extending through the case 336 to sensor circuitry therein.

Turning to the details of the transponder shown in FIG. 10A, the signal receiving antenna 328 is tuned to receive an RF signal at a frequency fA and pass it into the filtering and rectifying section 340. The output of the antenna 28 is connected to a bandpass filter 342 and an RF trap filter 343 tuned to frequency fB in the section 340. The bandpass filter 341 is desirable because the bandwidth of the antenna 328 will be wide due to the highly glossy tissue surrounding the implanted device 12. In the described example of the invention, frequency fA is 915 MHz and frequency fB is the second harmonic of frequency fA, or 1830 MHz. In this manner, the section 340 passes the 915 MHz frequency fA signal and filters out any 1830 MHz frequency signals. The filtered, received signal then flows to two different paths. In the first path, the signal flows through rectifying diode 348 and into a READ terminal of the microprocessor 342. In the second path, the signal flows directly into a first input of the harmonic generating and modulating section 344.

The harmonic generating and modulating section 344 generates harmonics of the frequency of the signal output from the section 340 and modulates the harmonic signals with digital data pulses representing patient information sensed by the implanted device 12.

In the disclosed embodiment, the second harmonic is employed. The harmonic generating and modulating section 44 has two inputs and one output. The first input is connected to section 340, as described above. The second input is connected to a SEND terminal of the microprocessor 342 which is a digital data output source. The output of the section 344 is connected to the signal transmitting filtering section 346 and signal transmitting antenna 330.

In one embodiment of the invention, the section 344 is a circuit comprising a high input impedance data switching transistor 50 (e.g., an N-type field effect transistor) and a harmonic generating diode 352. The positive side of the diode 352 receives the signal from the second path of the section 40 described above and also receives a signal from the drain of the switching transistor 350. As shown in FIG. 10A, the diode 352 may be optionally biased by an extremely low DC current (e.g., 0.1A) to increase the harmonic generation efficiency under very low RF power conditions. The negative side of the diode 352 is the output of the section 344. The source of the switching transistor 350 is connected through a resistor to the SEND terminal of the microprocessor 342 and to ground. The gate of the switching transistor 350 is connected directly to the SEND terminal.

FIG. 10B shows an alterative embodiment of the harmonic generating and modulating section 344. In this embodiment, the section 344 is a single PNP transistor 354 wherein the transistor emitter is connected to the signal from the second path of the section 40 and the collector is the output of the section 344. The base is connected through a resistor to the SEND terminal of the microprocessor 342 and through a capacitor to ground.

As noted above, the output of the harmonic generating and modulating section 344 is connected to the signal transmitting filtering section 346 and signal transmitting antenna 330. The section 46 is an RF trap filter turned to fa. The antenna 30 thus transmits a pulse code modulated signal at frequency fB, which is 1830 MHz in the described example of the invention. The second harmonic was selected for the frequency fB because it allows for ultra-low power re-radiation.

Of course, it should be understood that the section 344 generates other harmonics and sub-harmonics of frequency fA which are also suitable for re-radiation. Although the invention is described as employing a transmitting frequency which is a second harmonic of the receiving frequency, other harmonic frequencies are within the scope of the invention.

In the preferred embodiment of the invention, the antennas 328 and 330 are microstrip antennas. The filters 341, 343, 346 and the modulation circuitry can be implemented in the microstrip transmission line on the same substrate as the antennas 328 and 330. For example, the frequency trap filters 343, 346 can be implemented as microstrip stubs. A limiter can be incorporated into the microstrip transmission line associated with the antenna 328 to protect the transponder circuitry 26 against unusually high radiation levels. Either center feeds or offset feeds can be employed for the microstrip antenna design.

Figure 11A:
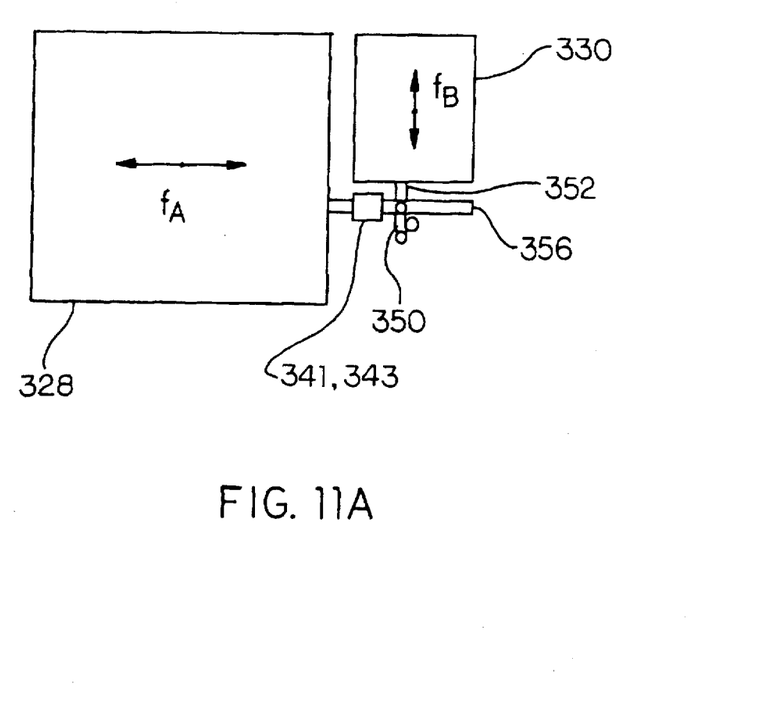
FIG. 11A is a diagrammatic representation of transponder antennas and selected transponder circuitry shown in FIG. 10A.

An important feature of the invention is the arrangement of the transponder microstrip antennas 328 and 330 with respect to each other and the manner in which they are grounded. FIG. 11A shows diagrammatically that the polarization of the antenna.

FIG. 11A also shows filters 341, 343 of the filtering and rectifying section 340 implemented in a microstrip transmission line 356. The antenna 330 is shown connected to the diode 352, which in turn, is connected to the switching transistor 350.

The microstrip antennas 328 or 330 also function as a DC ground by shorting the center of the antenna (either directly or through an inductive element) to a ground plate such as the implant's case. The symmetrical antenna center can be shorted because the wave impedance at this point is ideally zero. This grounding feature is desirable because many implanted devices use their cases as the DC ground for their circuit functions.

Figure 11B:
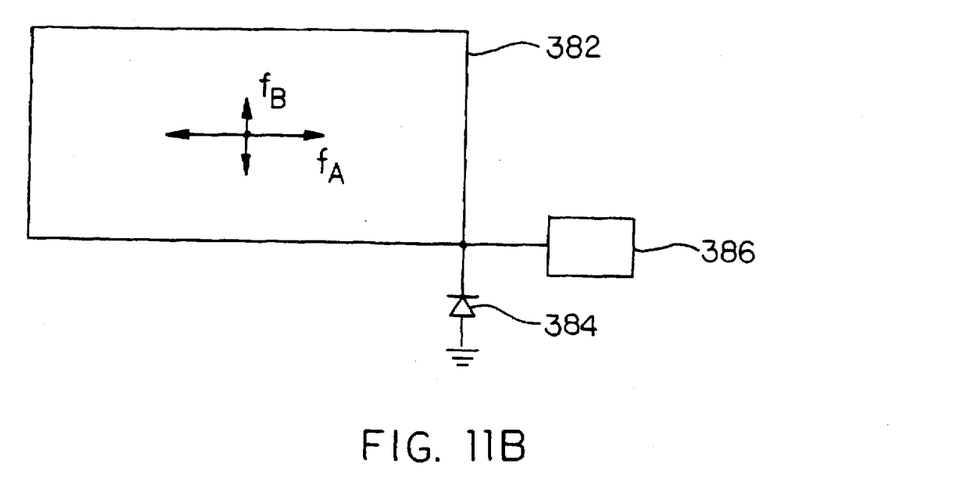
FIG. 11B is an alternative diagrammatic representation of transponder antennas and selected transponder circuitry suitable for use in FIG. 10A.

FIG. 11B shows an alterative antenna configuration which employs a single dual-frequency rectangular, corner-fed microstrip 382. This microstrip 382 resonates at frequency fA in the long direction and at frequency. fB in the orthogonal direction. Again, the two polarizations are orthogonal. The center of the rectangular microstrip is also shorted. In the embodiment described herein, the rectangle has a 2:1 dimensional ratio, reflecting the ratio between the two frequencies. Shunt diode 384 connected at the corner feed performs harmonic generation and detection. This alternative configuration simplifies the circuit necessary to perform these functions. Element 386 includes the filtering, biasing and switching circuitry.

To improve the reliability of the communications between the RPP 14 and the implanted device 12, the transmitting and receiving antennas in the RPP 14 are also orthogonally polarized with respect to each other in same manner as described above with respect to the transponder antennas. The signal received by the antenna in the circuitry 360 may be first down converted to a common frequency so that a commercially available heterodyne circuit chip can be employed for the remaining parts of the circuitry.

Application Ser. No. 322,852 further describes a preferred protocol which is not part of this invention. Briefly, to interrogate implant device 12, the remote control 10 sends an information request signal to the RPP 14 through the cellular telephone network or an equivalent PCN. The information request signal is received by the RPP 14 and converted into an interrogation signal. Then, the RPP's transmitting circuitry modulates the carrier frequency fA with the interrogation signal and transmits the modulated signal to the implanted device 12 at time t1.

The microprocessor 342 in the transponder circuitry 326 of the implanted device 12 receives the interrogation signal at its READ terminal at t2 which will be almost instantaneously after t1, when RF carrier signals are employed. In response, the microprocessor 342 sends out a digital data pulse stream (i.e., a condition information signal) at time t3 which contains the requested information. Time t3 is a discrete time period after t2.

At about time t3, the signal transmitted from the RPP's transmitting circuitry is no longer modulated by the interrogation signal. That is, the interrogation signal only modulates the RPP's carrier signal for a short time interval after time t1. Thus, at time t3, the signal from the second output path of the transponder's filtering and rectifying path 40 which flows directly into the harmonic generating and modulating section 344 is a pure carrier signal at frequency fA. This pure carrier signal is frequency doubled and modulated with the digital data pulse stream to create a modulated signal at frequency fz, containing the condition information. The RPP 14 receives this signal, demodulates it and sends it to the RPP's communication circuitry 362 for subsequent communication to the remote station. When the transponder circuitry 326 time-shares a microprocessor associated with the implanted device, the interrogation signal sent out by the RPP 14 "wakes up" the microprocessor circuitry. Thus, when an appropriate identification signal is received by the microprocessor, it becomes fully functional and ready to send out information signals related to monitored body conditions. Therefore, the modulation of the RPP's carrier frequency fA is for identification purposes only. This scheme acts as a double check so that the transponder circuitry 326 only returns a modulated information signal when the RPP 14 unequivocally desires to address the implanted device 12 associated with that particular patient. Of course, the RPP 14 will perform a first check against causing the implanted device 12 to falsely respond by checking that the information request signal received from the monitoring station 10 is directed to the associated implanted device 12. If the signal is not appropriate for the implanted device 12, the RPP 14 will not transmit any signal from the transmitting circuitry 358.

The interrogation routine described above allows the system described herein to be retrofitted to existing implanted devices. However, if it is desired to implement more sophisticated interrogation routines, the processor circuitry of the prior art implanted devices must be modified accordingly.

Another alterative interrogation routine dispenses with the need for a modulated interrogation signal. The microprocessors in implanted devices will "wake up" upon receiving a pure carrier signal. If the implanted device 12 employs such a microprocessor, it is only necessary for the remote station to send an information request signal to the RPP 14. In response to this signal, the RPP 14 sends out a pure carrier signal at frequency fA. This pure carrier signal wakes up the microprocessor and the interrogation routine continues in the same manner as described above. One disadvantage of this routine is that there is no double check protection against falsely waking up the microprocessor. Thus, the remote station 10 could potentially receive a condition information signal from the wrong patient.

Although the novel telemetry system is described as employing a frequency fB which is the second harmonic of frequency fA, wherein the frequency fA is 915 MHz, the scope of the invention includes any interrogating frequency fA and a responding frequency fB which is the same, a super harmonic or a sub-harmonic of the frequency fA. However, the use of a high carrier frequency such as 915 MHz enables the system to achieve a high communications data rate of about 100 kbps. This rate is over ten times greater than typical prior art telemetry data rates for implanted devices.

Although the invention has been described with reference to several particular embodiments, it is to be understood that these embodiments are merely illustrative of the application of the principles of the invention. For example, as cellular telephone technology evolves and further miniaturization occurs, it is expected that the telephone may be implemented along with, or as part of, the pacemaker. Moreover, instead of a full function cellular telephone, a reduced function device mode as a pager or a beeper may be used. Accordingly, the embodiments described in particular should be considered exemplary, not limiting, with respect to the following claims.

We claim:

1. A cardiac system comprising:
   A. a cardiac device including an implantable housing, said implantable housing having therein:
      (i) interface means for exchanging electrical signals with a patient's heart, said electrical signals including intrinsic signals from said heart indicative of intrinsic events and stimulation signals to said heart;
      (ii) control means coupled to said interface means for analyzing signals received from said heart and for generating corresponding output electrical signals; said control means being provided to generate said stimulation signals selected to provide therapy in accordance with a plurality of programmable parameters; and
      (iii) implanted transceiver means coupled to said control means for exchanging information over an RF channel, said information including said output signals and commands for modifying said programmable parameters;
   B. an external device having:
      (i) a cardiac portion including external transceiver means for exchanging information with said implanted transceiver means; and
      (ii) a communication portion coupled to said cardiac portion for exchanging said information and for establishing communication over a standard communications channel; and
   C. a remote control device disposed at a remote location from said external device, said remote control device including remote control communications means for establishing communications over said standard communications channel with said external device, said remote control device receiving said output signals from said external device over said standard communications channel and modifying an operation of said cardiac device by generating said commands.

2. The system of claim 1 wherein said standard communications network includes a cellular telephone system.

3. The system of claim 1 wherein said cardiac device is a pacemaker.

4. The system of claim 1 wherein said cardiac device is a cardioverter.

5. The system of claim 1 wherein said cardiac device is a defibrillator.

6. The system of claim 1 wherein said external device includes means for monitoring said cardiac device to detect an emergency, said external device responsive to said emergency establishing communication with said remote control device to obtain assistance.

7. The system of claim 6 wherein said external device includes means for locating said patient geographically, said external device transmitting location information to said remote control device.

8. The system of claim 1 wherein said external device receives status information from said cardiac device at regular intervals.

9. The system of claim 8 wherein said external device transmits said status information to said remote control device.

10. A cardiac stimulation system for applying therapy to a patient, said system comprising:
    a. an implantable cardiac stimulation device having means for sensing electrical activity in the heart of a patient, means for analyzing said electrical activity, means for generating first and second electrical stimulation signals for said heart to provide selectively one of a corresponding first therapy and a second therapy, means for sensing a change in a condition of the patient, means for automatically switching between said first and second therapies in response to said change in condition, and cardiac communication means for transmitting information corresponding to said switching of therapies; and
    b. an external device constructed and arranged for use by said patient, said external device including external communication means in communication with said cardiac communication means for receiving said information, and an annunciating means for annunciating to said patient when said therapies are switched.

11. The system of claim 10 wherein said external device includes a display means for displaying said annunciating signals.

12. The system of claim 10 wherein said annunciating signals are aural signals and wherein said external device includes a speaker for reproducing said aural signals.

13. The system of claim 10 wherein said external device further includes means for receiving patient data, said patient data being transmitted by said external communication means to said cardiac device for modifying at least one of said therapies.

14. The system of claim 13 wherein said means for receiving patient data includes a keyboard.

15. The system of claim 10 wherein said cardiac device includes means for deriving patient specific information from said sensed activity, and wherein said external device includes display means for displaying said patient specific information.

16. The system of claim 10 wherein said external device further includes further communication means for exchanging signals over a standard telephone network.

17. The system of claim 16 wherein said further communication means includes a cellular telephone.

18. The system of claim 10 wherein said external device further includes a keyboard for receiving input information and modifying means for modifying said operational parameters based on said input information.

19. The system of claim 10 further comprising means for geographically locating said patient.

20. The system of claim 19 wherein said locating means comprises a ground position indication system.

21. The system of claim 20 wherein said ground position indication system is disposed in said external device.

22. A method of providing cardiac stimulation therapy to a patient comprising the steps of:
    a. implanting in said patient a cardiac stimulation device;
    b. sensing cardiac activity with said cardiac stimulation device;
    c. providing an external device for said patient for monitoring said cardiac stimulation device;
    d. generating cardiac stimulation signals by said cardiac stimulation device for said heart based on sensed cardiac activity and a set of functional parameters;
    e. initializing said cardiac device using said external device; and
    f. transmitting information at regular intervals from said cardiac device to said external device, said information being related to said cardiac sensing and said functional parameters.

23. The method of claim 22 further comprising transmitting said information by said external device to a remote control device.

24. The method of claim 22 further comprising transmitting said modified functional parameters to said external device and to said cardiac stimulation device.

25. The method of claim 24 wherein said information is transmitted over a standard telephone line.

26. The method of claim 24 wherein said information is transmitted a cellular telephone system.

27. A cardiac stimulation system for applying therapy to a patient, said system comprising:
   a. an implantable cardiac stimulation device having means for sensing electrical activity in the heart of a patient, means for analyzing said electrical activity, means for generating first and second electrical stimulation signals for said heart to provide selectively one of a corresponding first therapy and a second therapy, means for switching between said first and second therapies in response to data from said patient indicative of a change in a condition of the patient, and cardiac communication means for receiving said data; and
   b. an external device constructed and arranged for use by said patient, said external device including data entry means for entering said data by said patient and external communication means in communication with said cardiac communication means for transmitting said data.

28. The system of claim 27 wherein said stimulation device includes sensing means for sensing a change in an internal condition of said patient and wherein said cardiac communication means sends information corresponding to said change in said internal condition to said external device.

29. The system of claim 28 wherein said external means includes an annunciator means for annunciating said information.

30. The system of claim 29 wherein said annunciating means is adapted to generate sounds.

31. The system of claim 29 wherein said annunciating means is adapted to generate a visual indication corresponding to said information.

32. The system of claim 29 wherein said external device includes a selector for selecting one of a plurality of choices by said patient, said choices being causally related to said information.

33. A method of providing cardiac stimulation therapy to a patient comprising the steps of:
   a. implanting in said patient a cardiac stimulation device;
   b. sensing cardiac activity with said cardiac stimulation device;
   c. providing an external device for said patient for monitoring said cardiac stimulation device;
   d. generating cardiac stimulation signals by said cardiac stimulation device for said heart based on sensed cardiac activity and a set of functional parameters;
   e. transmitting information at regular intervals or on request from said cardiac device to said external device, said information being related to said cardiac sensing and said functional parameters;
   f. transmitting said information from said external device to a remote control device; and
   g. modifying said functional parameters by said remote control device.

34. The method of claim 33 wherein said information is transmitted from said external device to said remote control device over a standard telephone line.

35. The method of claim 33 wherein said information is transmitted from said external device to said remote control device using a cellular telephone system.

36. The method of claim 33 wherein one of said cardiac stimulation device and said external device includes a patient locating system further comprising the step of locating a position of said patient with said patient locating system and transmitting said location to said remote control device.

37. The method if claim 36 further comprising the steps of determining when said cardiac activity indicates a dangerous condition of said patient and transmitting said location of said patient when said dangerous condition is indicated.

38. The method of claim 33 wherein said remote control device includes data logging means further comprising the step of logging said information with said data logging means.

* * * * *